May 28, 1974 D. A. HANNERS Plant Pat. 3,560
APPLE TREE
Filed March 8, 1973
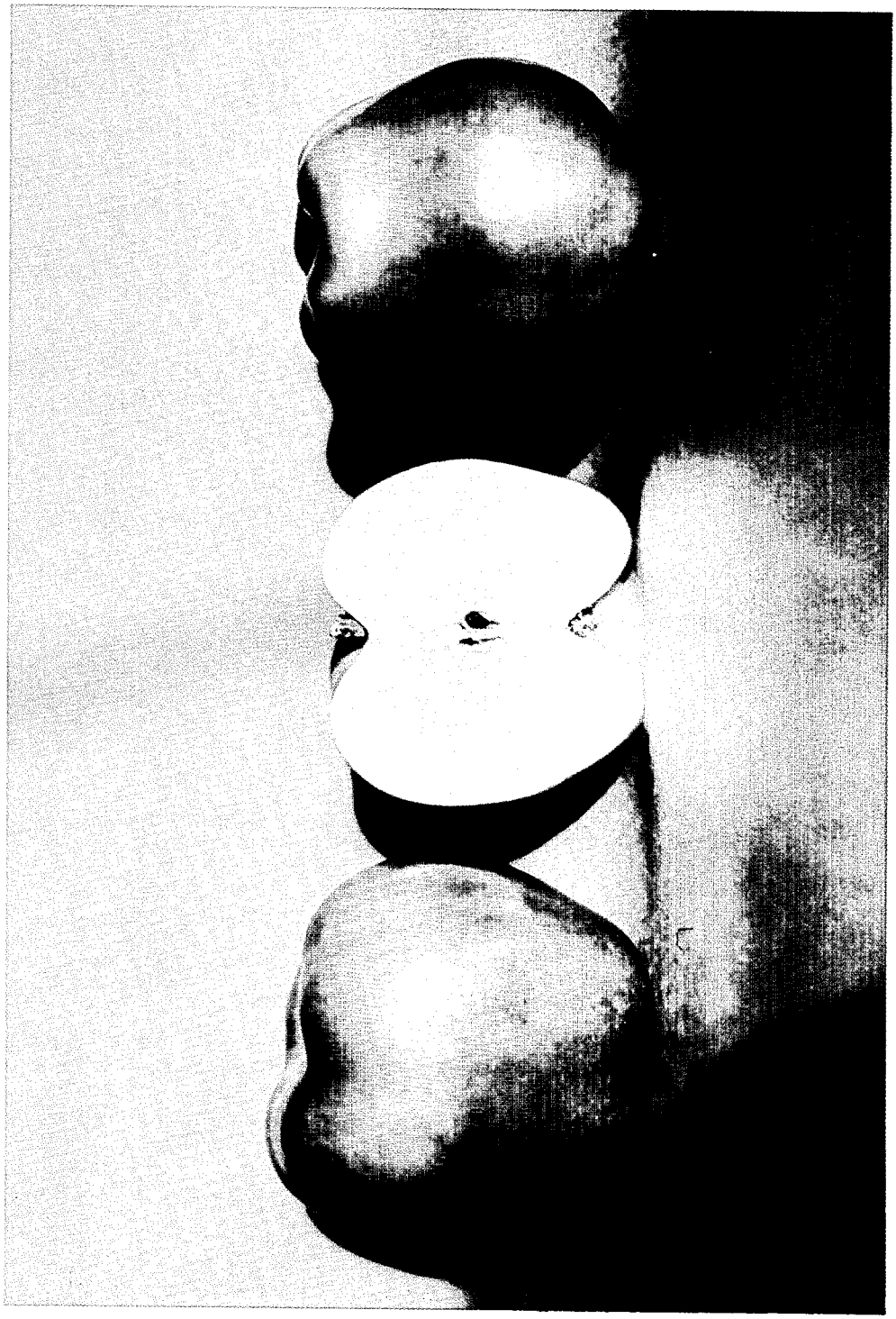

United States Patent Office

Plant Pat. 3,560
Patented May 28, 1974

3,560
APPLE TREE

Daniel A. Hanners, Hood River, Oreg., assignor to Stark Bro's Nurseries & Orchards Co., Louisiana, Mo.

Filed Mar. 8, 1973, Ser. No. 339,355
Int. Cl. A01h 5/03
U.S. Cl. Plt.—35 1 Claim The present invention relates to a new and distinct variety of apple tree which was discovered by me as a cultivated sport of the apple variety known as "Stark Jumbo" (unpatented) which occurred as a whole tree mutation selected from six rather similar trees of a group of sixty trees being propagated by me from scions cut from a "Stark Jumbo" tree, said discovery having been made by me in my orchard located at Hood River, Oregon.

At the time of my discovery aforesaid, I was conducting a routine inspection of my orchard, during the course of which my attention was attracted to six trees which bore fruit, having an attractive, nearly solid bright red blush over most of the surface of each fruit. These six trees were among a group of sixty trees being propagated from scions which I had taken from a "Stark Jumbo" tree which normally bore fruit having a yellowish green ground color with red stripes on only about half of the fruit surface. Other than the six trees of the group preferred to above, fifty-four bore poorly colored striped fruit typical of the "Stark Jumbo" variety. I immediately took steps to preserve the sport trees and kept them under close observation. In due course, I asexually reproduced the sport trees by budding the same in my orchard at Hood River, and selected the best for further propagations.

Continued observations and tests of the new sport and its progeny derived therefrom by budding as aforementioned, have conclusively convinced me that it is a new and improved variety, as evidenced by the fact that it resembles the parent variety "Stark Jumbo" in all respects except for the different and more attractive fruit color as referred to in the foregoing, and which distinguishes the same from its parent variety, as well as from all other apple varieties of which I am aware.

The accompanying drawing shows typical specimens of the fruit of my new variety, with one of the fruit specimens being shown in cross section, as depicted in color as nearly true as it is reasonably possible to make the same in a color illustration of this character. Since all other characteristics of the sport are similar to those of "Stark Jumbo," no further illustrations are needed, but for convenience, the new variety will be hereinafter more fully described.

The following is a detailed description of the new variety, with color terminology in acordance with Ridgway's Color Standards and Nomenclature (hereinafter abbreviated as (R)), Munsell Color Chart (hereinafter abbreviated as (M)), and the Horticulture Color Guide (hereinafter abbreviated as (HCG)), except where general color terms of ordinary dictionary significance are obvious:

Locality where grown and observed: Hood River, Oregon.

Parentage: Limib mutation or sport of "Stark Jumbo."

Dates of first and last pickings: About September 25 and October 5, respectively.

Tree: Medium large; medium vigorous; open; rapid growing; hardy; very productive; regular bearer.

*Trunk.*—Medium slender; smooth.

*Branches.*—Medium thickness; smooth; medium branching. Color (2 years old)—Maroon, Plate I, Color No. 3, tone m (R). Lenticels—Medium number; small.

*Leaves.*—Large; wide; long; oval; abruptly pointed; thick; rugose. Length—About 3 inches. Width—From about 2 inches to 2½ inches. Color—Dark Yelowish Green, Hue 2.5 G 4/6(M). Petiole—Long; medium thickness.

Flowers: Medium early; medium large.

*Dates of first and full bloom.*—About April 15 and April 25, respectively.

*Color.*—White, with tinge of Deep Pink, Hue 2.5 R 6/11 (M).

Fruit:

*Maturity when described.*—Eating ripe (about November 6).

*Size.*—Uniform. Axial diameter—From about 4½ inches to 5 inches. Transverse diameter—From about 4½ inches to 5 inches. Shape—Ovoid; conical; ribbed.

*Cavity.*—Unsymmetrical; rounded toward apex; acute; undulate. Depth—About 1 inch. Breadth—About 2 inches. Markings—Color—Light Grayish Olive, Plate XLVI, color No. 21'''', tone b (R).

*Basin.*—Unsymmetrical; wide flaring; undulate; glabrous. Depth—About 1 inch. Breadth—About 1¾ inches. Markings—None.

*Stem.*—Medium stout. Length—about ¾ inch. Breath—about 5/32 inch. Markings—None.

*Calyx.*—Partially open; segments persistent; broadly lanceolate; about ¼ inch long; separated; reflexed from base at apex; both outer and inner surfaces pubescent.

*Eye.*—Large; open.

*Skin.*—Tough; glossy; waxed. Dots—Obscure; few; small; depresed; ruptured; circular. Color of dots—Tilleul Buff, Plate XL, color No. 17''', tone f (R). Distribution of dots—Even. Ground color—Charteuse Green, Plate 663, page 90, Vol. 1 (HCG). Color markings—Blushed; bright; color—Cardinal Red, Plate 882, page 168, Vol. 2 (HCG), Bloom—Wanting. General color effect—Bright red blush covering about 80% of the surface.

*Flesh.*—Rather juicy. Color—Satiny white, with greenish tint. Texture—Firm; tender; fine; crisp. Flavor—Subacid. Quality—Good.

*Core.*—Median. Bundle area—Large; cordate; symmetrical at base. Halves of area—Equal. Bundles—Inconspicuous; in two whorls; color—green. Alternate bundle—Distant from calyx. Core lines—Clasping. Calyx tube—Glabrous; cone-shaped; depth (entire)—about ⅞ inch. Styles—Wanting. Stamens—Median; in one whorl. Seed cells—Closed. Cell walls—Distant; thin; tough. Length—About ⅞ inch; breath—about ½ inch. Longitudinal section—Oval; obtuse at apex. Surface—Fissured; tufted. Cross section—Broad.

Seeds: Usually 7; no more than 2 per cell.

*Length.*—About 5/16 inch.

*Breadth.*—About 7/32 inch.

*Form.*—Obtuse.

Use: Local; culinary.

Keeping quality: Medium good; about 90 days in ordinary storage.

Insect and disease resistance: Good insect resistance and good resistance to scab and mildew, as determined from comparison with other apple varieties grown under the same conditions at Hood River, Oregon.

I claim:

1. A new and distinct variety of apple tree, substantially as herein shown and described, characterized particularly as to novelty by its resemblance in all respects except fruit color to the variety known as "Stark Jumbo," but differing from the latter by a bright solid red blush on almost all of the surface of each fruit, as compared with the typical yellowish green ground color having red stripes extending over only half of the fruit surface of the fruit of "Stark Jumbo."

No references cited.

ROBERT E. BAGWILL, Primary Examiner